(12) United States Patent
Guillermo (10) Patent No.: US 7,955,304 B2
(45) Date of Patent: Jun. 7, 2011

(54) INJECTOR (75) Inventor: Carlos Guillermo, Los Osos, CA (US)

(73) Assignee: SHL Group AB, Nacka Strand (SE)

( * ) Notice: Subject to any disclaimer, the term of this patent is extended or adjusted under 35 U.S.C. 154(b) by 1256 days.

(21) Appl. No.: 11/182,060

(22) Filed: Jul. 15, 2005

(65) Prior Publication Data

US 2007/0021720 A1    Jan. 25, 2007

(51) Int. Cl.
*A61M 5/20* (2006.01)

(52) U.S. Cl. .................................. 604/137; 604/134

(58) Field of Classification Search ............ 604/165.02, 604/208, 134–137
See application file for complete search history.

(56) References Cited

U.S. PATENT DOCUMENTS

| | | | |
|---|---|---|---|
| 5,300,030 A * | 4/1994 | Crossman et al. | 604/136 |
| 5,620,421 A * | 4/1997 | Schmitz | 604/135 |
| 2004/0039336 A1 * | 2/2004 | Amark et al. | 604/136 |
| 2005/0016528 A1 | 1/2005 | Aslin et al. | |
| 2006/0258990 A1 * | 11/2006 | Weber | 604/208 |

FOREIGN PATENT DOCUMENTS

| | | |
|---|---|---|
| EP | 0824922 | 2/1998 |
| FR | 2519866 | 7/1983 |
| WO | 2005/011780 | 2/2005 |
| WO | WO 2005011780 A2 * | 2/2005 |

OTHER PUBLICATIONS

Partial European Search Report completed Sep. 12, 2005 in corresponding European Patent Application No. EP05106504.

* cited by examiner

*Primary Examiner* — Nicholas D Lucchesi
*Assistant Examiner* — Laura A Bouchelle
(74) *Attorney, Agent, or Firm* — Potomac Patent Group PLLC (57) ABSTRACT

The present invention relates to a method of operating an injection device, which device comprises a medicament cartridge and a needle attached to said cartridge, means for automatic penetration of needle, injection of medicament and withdrawal of needle, comprising the steps of initiating a penetration sequence, followed by an injection sequence and followed by a withdrawal sequence, wherein a previous sequence triggers a subsequent sequence, and wherein the subsequent sequence is triggered before the previous sequence has ended.

13 Claims, 7 Drawing Sheets

INJECTOR

TECHNICAL FIELD

The present invention relates to an injector, and in particular an injector having several automatic functions.

BACKGROUND OF THE INVENTION

There are many injectors on the market where the aim is to have high degrees of functionality and automatic features, such as in connection with penetration, injection, setting of dose, priming and covering of the needle after use. At the same time there is a demand on robustness, repeatability and reliability regarding the function, which sometimes might be difficult to meet when dealing with complex multi functions involving many interacting components. When there further are demands on low production costs, especially for devices that are to be used only once, the picture becomes even more complex.

There are in the patent literature numerous solutions to injection devices, the bulk of which never enter the market due to that they do not meet the demands in one way or the other. There is therefore a continuous search for solutions that provide the desired functions that at the same time fulfill the functional and/or economical demands.

Many devices having multi-functions that work in sequence, such as for example penetration, followed by injection, followed by withdrawal, have a subsequent sequence triggered at the end of a previous sequence, for example when the needle has reached full penetration depth, the injection sequence is triggered.

The drawback with this solution, especially when several components are interacting with each other in order to perform the sequences and the triggering of them, is that the tolerance and functional demands are increased in order to ensure that the subsequent sequence is really triggered at the end of the previous sequence. Should there be a tolerance error or a mismatch between two interacting components for triggering a subsequent sequence, the previous sequence will come to an end without triggering the next sequence. This may lead to a fatal situation if for example the injection of medicament is not performed.

In view of cost efficiency, high tolerance demands in order to achieve the desired chain of functions, are not advantageous, in particular when mass-producing injection devices.

BRIEF DESCRIPTION OF THE INVENTION

The aim of the present invention is to provide an injector that fulfils the demands that are put on such devices both regarding functionality, reliability and low cost.

According to a main aspect of the invention it is characterized by the features of claim 1. Further advantageous features are subject of the dependent claims.

The present invention is characterized by a method of operating an injection device, which device comprises a medicament cartridge and a needle attached to said cartridge, means for automatic penetration of needle, injection of medicament and withdrawal of needle, comprising the steps of initiating a penetration sequence, followed by an injection sequence and followed by a withdrawal sequence, wherein a previous sequence triggers a subsequent sequence, and wherein the subsequent sequence is triggered before the previous sequence has ended.

The advantage with the method according to the present invention is for one that a subsequent sequence of operation of the injector is not triggered at the end of a previous sequence. This provides an increased reliability regarding ensuring that a subsequent sequence is triggered by a previous sequence, without increasing the tolerance and functional demands on the interacting components.

The triggering of a subsequent sequence may preferably in an end range of movement of components performing the previous sequence.

The solution provides a cost effective multi-function device comprising a safe and reliable chain of sequences, thus ensuring that the user receives a proper dose of medicament each time the device is used.

These and other features and advantages with the present invention will become apparent from the following detailed description and the drawings

BRIEF DESCRIPTION OF THE DRAWINGS

In the following detailed description, reference will be made to the drawings, of which

DETAILED DESCRIPTION OF THE INVENTION

Figure 1:
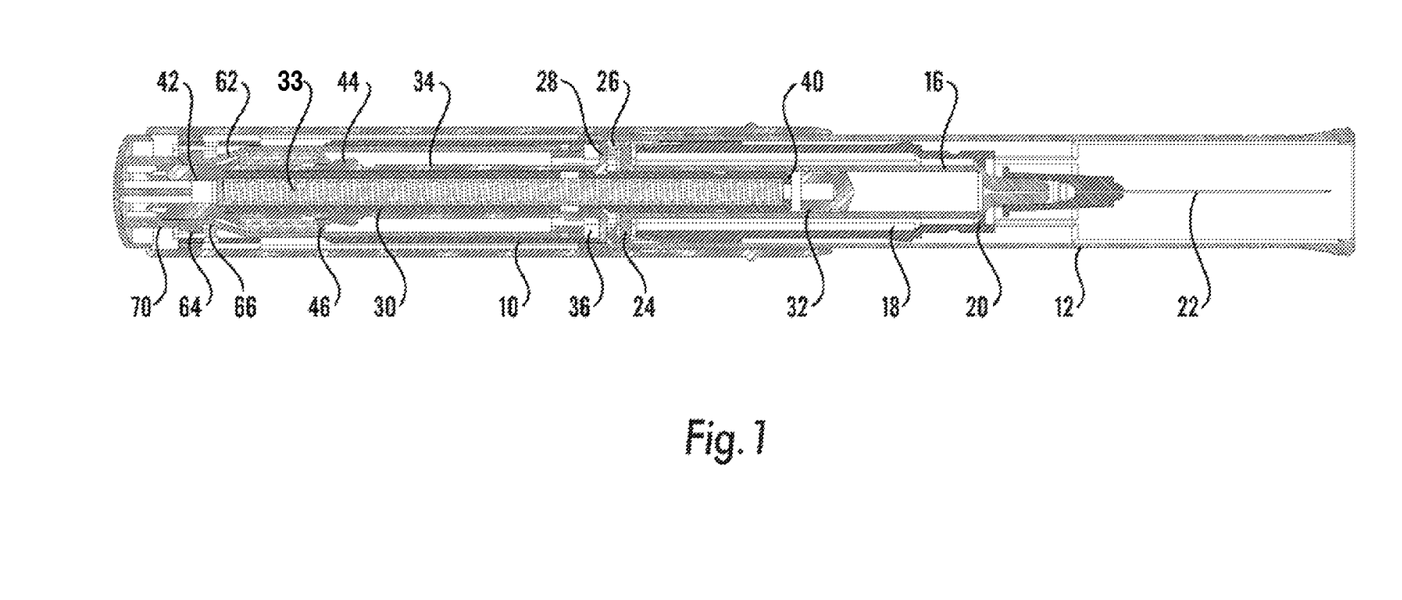
FIG. 1 is a longitudinal cross-section of an embodiment of the present invention.
Figure 2:
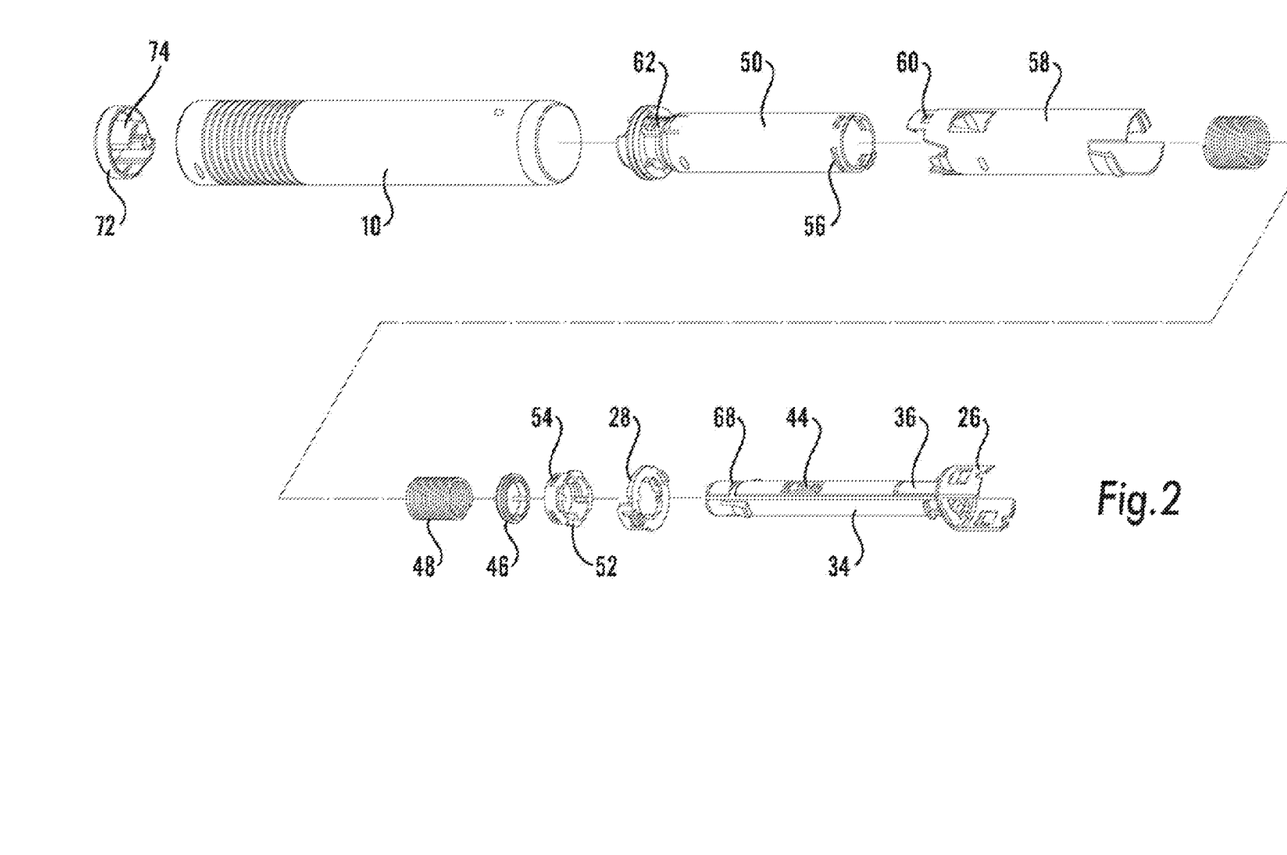
FIGS. 2-3 are exploded views of the injector of FIG. 1, FIGS. 4-7 show different functional steps of the device of FIG. 1.
Figure 3:
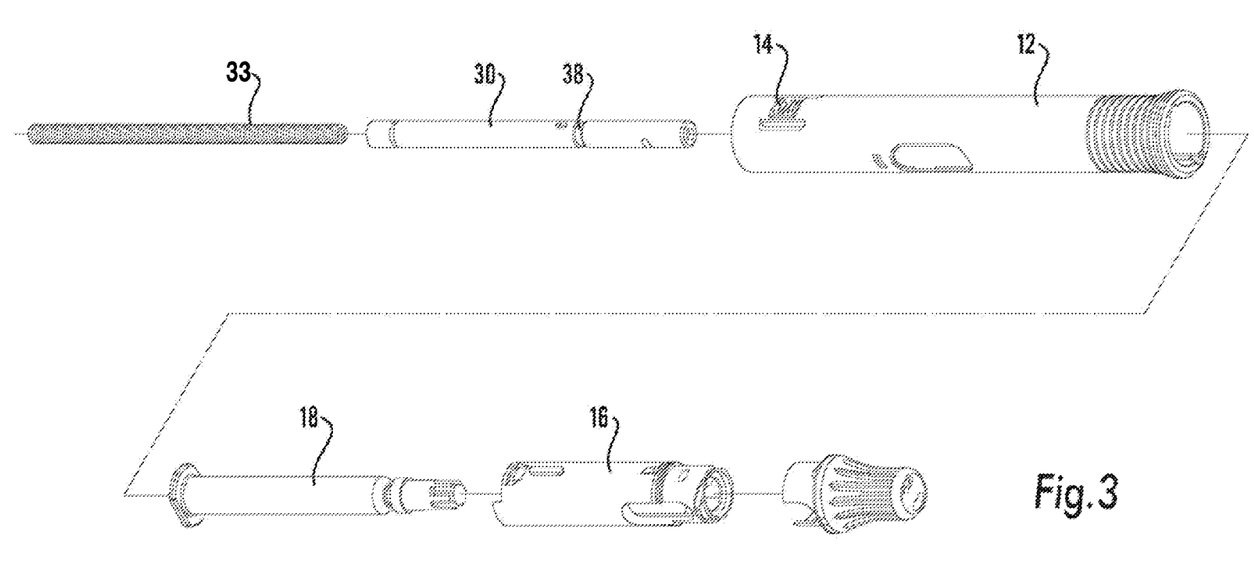

The device according to the figures comprises a generally tubular outer housing 10. In the front end of the housing, to the right in FIG. 1, a generally tubular needle shield 12 is arranged slidably in the outer housing. When in the non-extended position the needle shield is held in place by protrusions 14 on the outer surface co-operating with ledges (not shown) on the inner surface of the housing. Inside the needle shield in the front area of the device a syringe carrier 16 is arranged. Inside the syringe carrier a syringe 18, containing medicament, is arranged. The syringe is prevented from moving forward by a circumferential ledge 20. The front end of the syringe is arranged with attachment means for attaching a needle 22 to the syringe. The rear end of the syringe is seated with its flange 24 in a holder 26. Adjacent the holder an injection release ring 28 is arranged, which will be described in more detail below. A plunger 30 extends into the syringe with one end adjacent a stopper 32. The rear end of the plunger is surrounded by an activation housing 34 which is snap-fitted to the syringe holder. The activation housing is arranged with flexible tongues 36, where each tongue is arranged with inwardly directed ledges. In the initial state, these ledges are positioned in a circumferential groove 38 on the plunger 30. The tongues and ledges are held in this position by the injection release ring 28. Inside the plunger an injection spring 33 is arranged compressed between a front wall 40 of the plunger 30 and a wall part 42 of the activation housing 34. The activation housing is further arranged with outwardly extending protrusions arranged on flexible arms 44. Abutting the protrusions is a retraction release ring 46, which will be described closer below. A spring 48, hereafter named penetration spring, is arranged between the retraction release ring 46 and a penetration sleeve 50. At the front end of the penetration sleeve, a retraction spring retainer 52 is snap fitted with the penetration sleeve 50 by outwardly directed protrusions 54 having a straight part and a ramped part, extending into recesses 56 of the sleeve. Outside the penetration sleeve a lockout sleeve 58 is arranged. At the rear part of the lockout sleeve 58 recesses 60 are arranged adjacent flexible arms 62 of the penetration sleeve, which arms are arranged with outwardly extending protrusions 64 as well as inwardly extending ledges 66. In the initial position these ledges are in contact with a wall of a circumferential groove 68 on the plunger. The upper part of the arms is further arranged with inclined surfaces 70 At the upper end of the housing an activation button 72 is slidably arranged, having inwardly extending parts 74, which are arranged with inclined surfaces facing the inclined surfaces 70 of the arms 62.

Figure 4A:
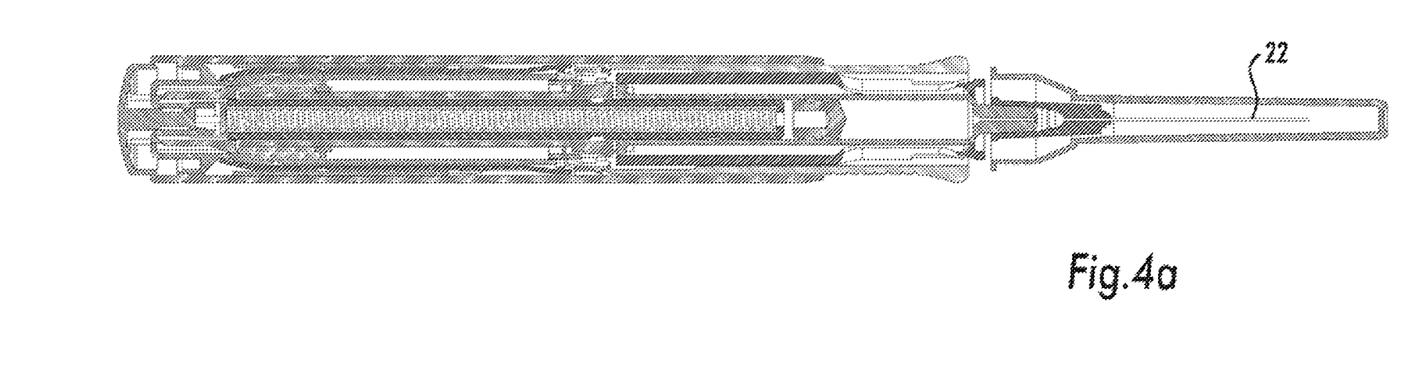
Figure 4B:
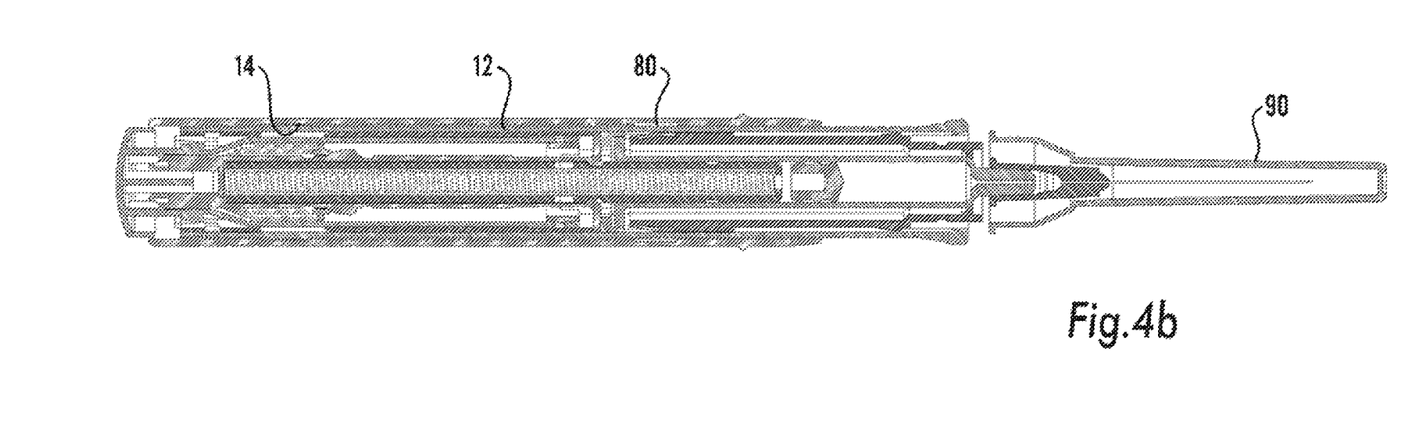
Figure 5A:
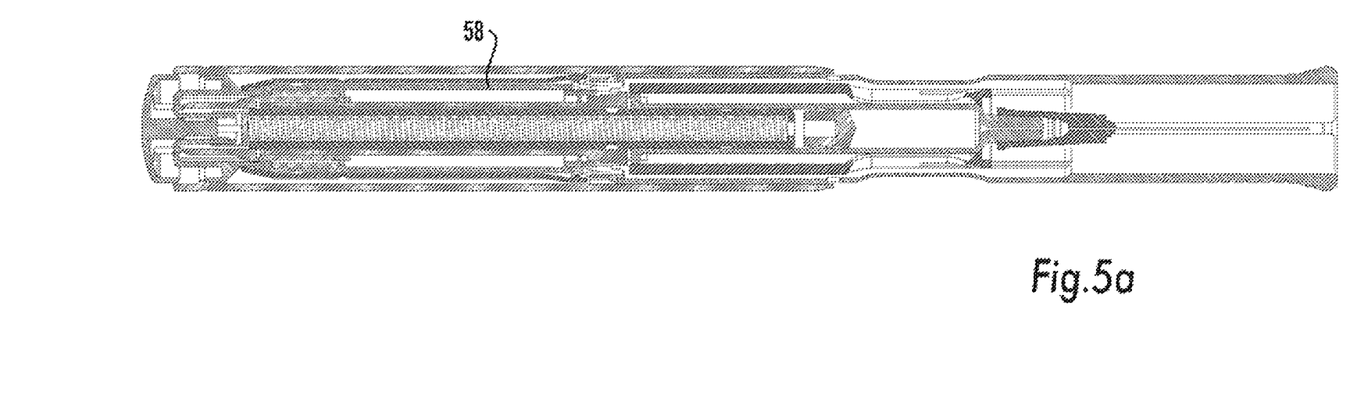
Figure 5B:
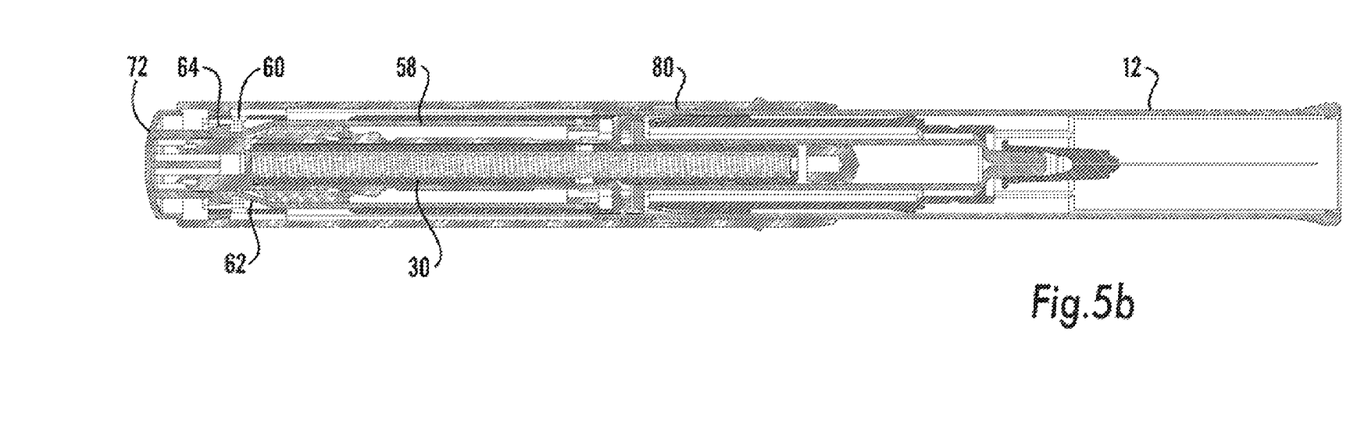

The device is intended to function as follows. When in the initial position the needle shield 12 is pushed inside the housing 10 and held in place by the protrusions 14 acting against the ledge of the housing, FIG. 4b. The device is delivered with a protective cap 76 inserted into the front end of the needle shield surrounding the front end of the syringe 18 with its syringe cap 78. The protective cap is removed, whereby the syringe cap is also removed, and a needle 22 is attached to the syringe. The needle shield 12 is then pushed manually forward until the protrusions 14 of the needle shield enter a recess 80 on the inner surface of the housing 10, FIG. 5b. The protrusions have such a configuration that they are able to slide over the ledge when the needle shield is extended but prevent a pushing in of the needle shield when they have entered the recess. The forward movement of the needle shield pushes a protective needle cap 90 off the needle.

The device is now ready to use. The user places the end of the needle shield 12 against the injection site and presses the push button 72. The pressing of the needle shield 12 causes it to move a short distance inwards until the protrusions 14 of the needle shield abut the upper wall of the recess 80. This movement causes the lockout sleeve 58 to be moved the same short distance since the upper end of the needle shield 12 in the extended position is in contact with the lower end of the lockout sleeve 58.

If the device is withdrawn from the injection site the lockout sleeve and the needle shield are moved back to initial position.

The movement of the lockout sleeve causes its recesses 60 to be positioned outside of the outwardly extending protrusions 64 of the arms 62 of the penetration sleeve 50, which enables the button 72 to be depressed whereby the inclined surfaces of the inwardly extending parts act on the inclined surfaces 70 of the arms 62, causing them to move radially outwards. This is not possible when the lockout sleeve 58 has not been moved since the protrusions of the arms then abut the inner surface of the lockout sleeve.

Figure 6A:
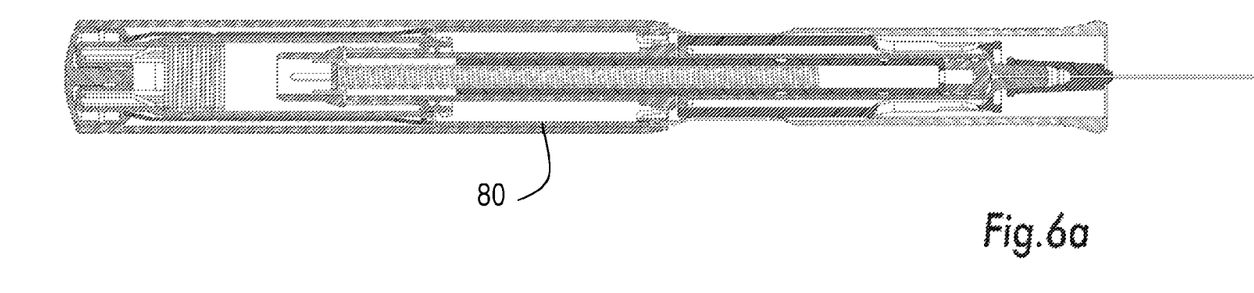
Figure 6B:
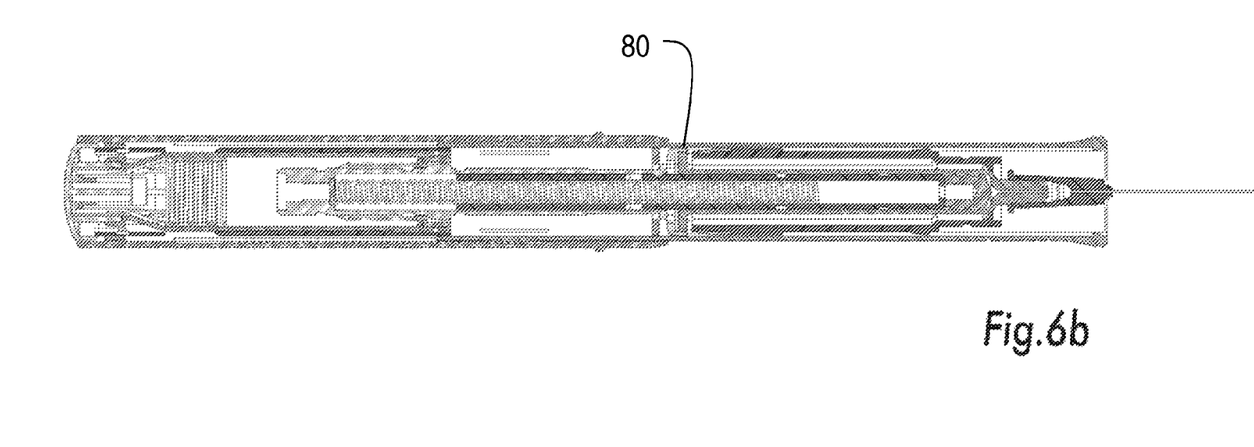

When the arms move radially outwards the inwardly directed ledges 66 of the arms 62 are moved out of contact with the circumferential groove 68 of the activation housing 34 which then is moved forward by the penetration spring 48 acting on the retraction release ring 46 which is held in place relative the activation housing 34 by the protrusions 44. Thus both the activation housing 34, the plunger 30 arranged inside the activation housing, the syringe carrier 16 connected to the activation housing, the injection release ring 28 and the syringe 18 arc moved forward causing a penetration of the needle into the injection site, FIG. 6.

At a certain depth the injection release ring 28 is stopped by the engagement of protrusions on its flexible arms into slots on the shield, which frees the flexible tongues 36 because they pass the ring due to the continued movement of the activation housing 34. The freeing of the tongues cause them to flex outwards radially, whereby the inwardly directed ledges are moved out of contact with the groove 38 on the plunger 30. The movement of the activation housing 34, and thus the penetration, is stopped when the retraction release ring 46 contacts the retraction spring retainer 52.

However the plunger is now free to move by the force of the injection spring 33, whereby it pushes on the stopper 32 and an injection is performed. The movement of the plunger in relation to the activation housing 34 causes the upper end of the plunger to pass the protrusions 44 of the activation housing, whereby they are capable of collapsing inwards.

Figure 7A:
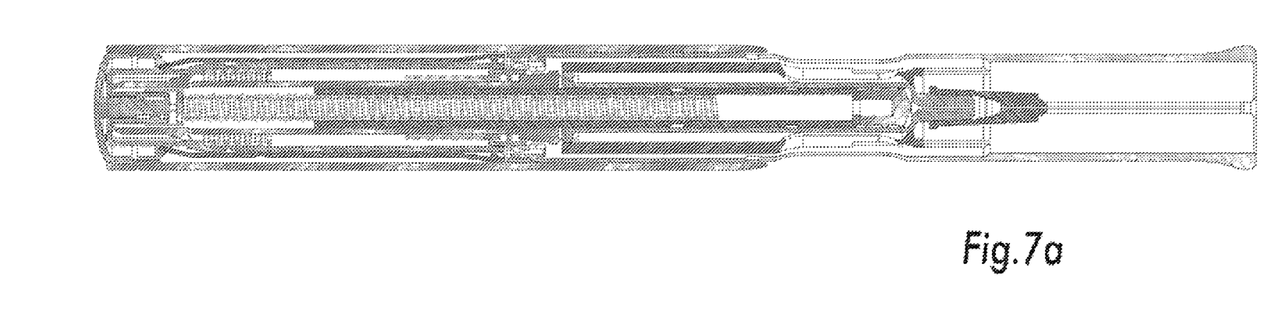
Figure 7B:
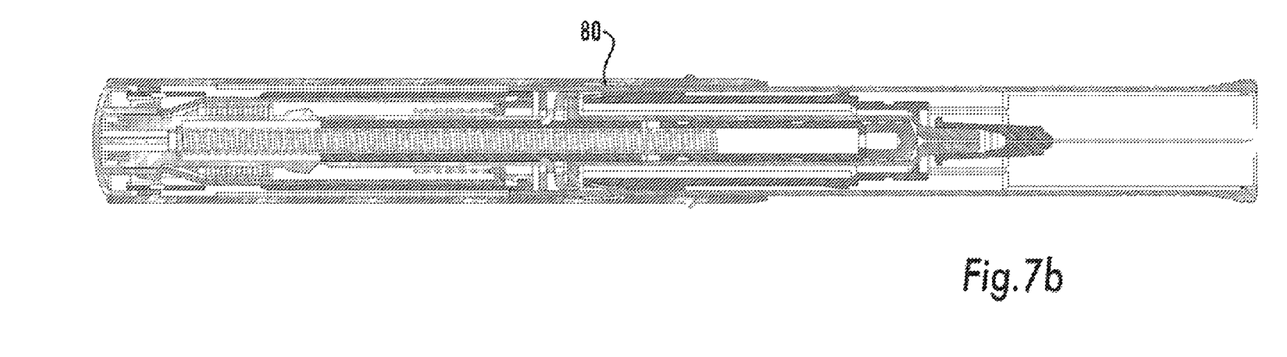

The collapsing causes the retraction release ring to pass the protrusions 44 and to be pushed downwards by the retraction spring 48. This causes the syringe carrier 16 to be pulled into the housing via the retraction spring retainer at near end of injection stroke, and thus the needle to be retracted, FIG. 7. The injection is now completed and the needle is protected inside the housing.

It is to be understood that the embodiment described above and shown in the drawings is to be regarded only as a non-limiting example of the invention and that it may be modified within the scope of the patent claims.

The invention claimed is:

1. Method of operating an injection device, which device comprises a housing, a needle shield arranged inside the housing for allowing attachment of a needle to the cartridge, a medicament cartridge and a needle attached to said cartridge, means for an automatic penetration of the needle, means for an automatic injection of medicament and means for an automatic withdrawal of needle, and a single-component joint activation housing having a penetration trigger means configured to initiate an automatic penetration sequence, an injection trigger means configured to initiate an automatic injection sequence, and a withdrawal trigger means configured to initiate an automatic needle withdrawal, comprising the steps of initiating a penetration sequence, followed by an injection sequence and followed by a withdrawal sequence, wherein a previous sequence triggers a subsequent sequence, the subsequent sequence is triggered before the previous sequence has ended, and withdrawal comprises displacement of the needle without displacement of the needle shield that is arranged inside the housing.

2. Method according to claim 1, wherein the first sequence is triggered by manual operation.

3. Method according to claim 2, wherein the manual operation comprises acting on a component on the device.

4. Method according to claim 2, wherein the manual operation comprises pressing the device against the injection site.

5. Method according to claim 3, wherein the sequence of manual operation is to first press against injection site and then act on a component of the device.

6. Injection device comprising a housing, a needle shield, a medicament cartridge and a needle attached to said cartridge, means for an automatic penetration of the needle, means for an automatic injection of medicament and means for an automatic withdrawal of the needle, and a single-component joint activation housing having penetration trigger means for initiating an automatic penetration sequence, injection trigger means configured to initiate an automatic injection sequence, and withdrawal trigger means configured to initiate an automatic needle withdrawal, wherein said trigger means are designed such that a subsequent sequence is triggered before the previous sequence has ended, and withdrawal comprises displacement of the needle without displacement of the needle shield, and the needle shield is arranged inside the housing for allowing attachment of a needle to the cartridge.

7. The injection device of claim 6, wherein the needle shield comprises protrusions configured to enter a recess on an inner surface of the housing when the needle shield is manually pushed forward for covering the needle.

8. The injection device of claim 6, wherein the automatic needle penetration means comprises an activation button, a penetration spring, a penetration sleeve arranged to interact with the needle shield, and a lockout sleeve arranged to interact with the penetration sleeve; and the penetration sleeve is arranged to interact with the penetration trigger means when the needle shield is pushed against an injection site such that the activation button is enabled to be depressed for initiating the penetration sequence.

9. The injection device of claim 6, wherein the medicament injection means comprises an injection release ring, a plunger, and an injection spring; and the injection release ring is arranged to interact with the injection trigger means for initiating the injection sequence.

10. The injection device of claim 6, wherein the withdrawal means comprises a retraction release ring and a retraction spring; and the retraction release ring is arranged to interact with the withdrawal trigger means for initiating the withdrawal sequence.

11. The injection device of claim 6, wherein the penetration trigger means is a circumferential groove.

12. The injection device of claim 6, wherein the injection trigger means is flexible tongues having inwardly directed ledges.

13. The injection device of claim 6, wherein the withdrawal trigger means is flexible arms having inwardly directed ledges having outwardly extending protrusions.

* * * * *